United States Patent [19]

Kawada et al.

[11] Patent Number: 6,160,014
[45] Date of Patent: Dec. 12, 2000

[54] METHOD FOR CONTROLLING ACARINA

[75] Inventors: Hitoshi Kawada, Funabashi; Yasuyori Tanaka, Toyonaka, both of Japan

[73] Assignee: Sumitomo Chemical Company, Ltd., Osaka, Japan

[21] Appl. No.: 09/168,889

[22] Filed: Oct. 9, 1998

[30] Foreign Application Priority Data

Oct. 9, 1997 [JP] Japan ................................ 9-277425

[51] Int. Cl.⁷ .................................................. A01N 37/12
[52] U.S. Cl. ........................................ 514/535; 514/537
[58] Field of Search ................................ 514/535, 537

[56] References Cited

U.S. PATENT DOCUMENTS 5,698,591  12/1997  Mori et al. .......................... 514/535

FOREIGN PATENT DOCUMENTS

| 57-156407 | 9/1982 | Japan . |
|---|---|---|
| 3083904 | 4/1991 | Japan . |
| 4208202 | 7/1992 | Japan . |
| 08319202 | 12/1996 | Japan . |
| 8319202 | 12/1996 | Japan . |

OTHER PUBLICATIONS

Chemical Abstracts, vol. 98, No. 9, Feb. 28, 1983, Columbus, Ohio, U.S., Abstract No. 67132, Sumitomo Chemical Co., Ltd., Japan: "Trifluromethanesulfonanilides as insecticides"—XP002092243 abstract & JP 57 156407.

Abstract of JP 08 319 202, Sumitomo Chemical Co., Ltd. "Cheyletiellidae killing agents—contain e.g. anilide cpd. Prepd. By reacting aniline derivative with trifluoromethane sulphonyl halide", XP002092244, Derwent, Publications, Ltd., London, GB; AN97–073051.

*Primary Examiner*—Jose' G. Dees
*Assistant Examiner*—Alton Pryor

[57] ABSTRACT

A method for controlling acarina which comprises setting a tablet(s) obtainable by pressing 2-methoxycarbonyl-4-chlorotrifluoromethanesulfonanilide or by pressing a composition containing 2-methoxycarbonyl-4-chlorotrifluoromethanesulfonanilide and a vehicle(s) in a small space such as drawers, a closet, a lumber room, etc.

7 Claims, No Drawings

METHOD FOR CONTROLLING ACARINA

FIELD OF THE INVENTION

The present invention relates to a method for controlling acarina.

BACKGROUND ART

It is known that 2-methoxycarbonyl-4-chlorotrifluoromethanesulfonanilide, shown with its chemical structure below:

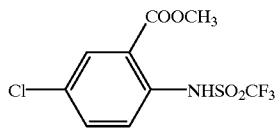

can be used for controlling acarina based upon Japanese Laid-open Patent No. hei-8-319202A.

SUMMARY OF THE INVENTION

The present invention provides a method for controlling acarina, especially indoor-inhabiting mites.

According to the present invention, it is an effective method for controlling acarina to set a tablet(s) obtainable by pressing 2-methoxycarbonyl-4-chlorotrifluoromethanesulfonanilide or by pressing a composition containing 2-methoxycarbonyl-4-chlorotrifluoromethanesulfonanilide and a vehicle(s) in a small space.

Moreover, the present invention provides an acaricidal tablet obtainable by pressing 2-methoxycarbonyl-4-chlorotrifluoromethanesulfonanilide or by pressing a composition containing 2-methoxycarbonyl-4-chlorotrifluoromethanesulfonanilide and vehicle.

DETAILED DISCLOSURE OF THE INVENTION

The tablet used for controlling acarina in the present invention contains 2-methoxycarbonyl-4-chlorotrifluoromethanesulfonanilide. A tablet obtainable by pressing 2-methoxycarbonyl-4-chlorotrifluoromethanesulfonanilide solely may be used, but it is also standard to use a tablet(s) obtainable by pressing a mixture of 2-methoxycarbonyl-4-chlorotrifluoromethanesulfonanilide and a suitable vehicle(s).

The vehicles used for producing the tablets can contain sublimative insecticides such as camphor, naphthalene, trioxane and p-dichlorobenzene, etc. as well as the common vehicles for producing tablets such as dextrin, crystallized cellulose, calcium hydrogenphosphate, calcium carbonate, starch, lactose, etc. In the case of using sublimative insecticides as vehicles, acarina are controlled by 2-methoxycarbonyl-4-chlorotrifluoromethanesulfonanilide and it is expected that the controlling effect against fabric pest insects, which may be hard to control by using 2-methoxycarbonyl-4-chlorotrifluoromethanesulfonanilide solely, can be increased.

The tablet used in the present invention can contain, if necessary, auxilaries for producing tablets such as lubricants (talc, stearic acid, calcium stearate, liquid paraffin, and so on) in addition to 2-methoxycarbonyl-4-chlorotrifluoromethanesulfonanilide or a mixture of 2-methoxycarbonyl-4-chlorotrifluoromethanesulfonanilide and a vehicle(s). The tablet can contain other insecticidal/acaricidal components, synergists and/or fungicide.

The amount of 2-methoxycarbonyl-4-chlorotrifluoromethanesulfonanilide in the tablet is usually 0.5 to 100 wt % and the tablet can be prepared by pressing under a pressure of usually 0.5 to 10 kg/cm$^2$.

According to the present invention, the above tablet(s) is/are where in a small space for controlling acarina. The small space set tablet(s) are set are generally less than 50 m$^3$ and close space. It is exemplified by a chest, a closet, a lumber room, cases (doll case, specimen case, clothing case, etc.), the inside of a doll, a stuffed doll, bedclothes ("futon" cotton, pillow, etc.) and so on. In the case of using the tablet in a storeroom, closet or lumber room, it is convenient that the tablet is put in a suitable container for hanging. In the case of using the tablet in a chest, the tablets are usually put in drawers. The amount of 2-methoxycarbonyl-4-chlorotrifluoromethane-sulfonanilide used is usually 0.1 to 200 g per 1 m$^3$ of the small space.

The acaricidal method of the present invention is especially effective on indoor inhabiting mites, for example, Pyroglyphidae such as American house dust mite (*Dermatophagoides farinae*), *Dermatophagoides pteronyssnus* and so on, Acaridae such as *Lardoglyphus konoi*, common grain mite (*Tyrophagus putrescentiae*), brown legged grain mite (*Aleuroglyphus ovatus*), Glycyphagidae such as *Glycyphagus privatus, Glycyphagus domesticus*, groceries mite (*Glycyphagus destrutor*) and so on, Chortoglyphus spp., Cheyletidae such as *Chelacaropsis moorei, Chelacaropsis malaccensis, Cheyletus fortis, Cheyletus eruditus, Chelatomorpha lepidopterorum* and so on, Macronyssidae such as *Ornithonyssus bacoti, Ornithonyssus sylviarum, Dermanyssus gallinae, Dermanyssus hirundinis* and so on, Halpochthonius spp., Pyemotes spp., itch mite and so on.

EXAMPLES

Below, the present invention will be explained in detail by examples.

The production examples of the tablet used for controlling acarina in the present invention are shown.

Production Example 1

2-methoxycarbonyl-4-chlorotrifluoromethanesulfonanilide is pressed under a pressure of 5 kg/cm$^2$ to give a tablet.

Production Example 2

A mixture of five parts by weight of 2-methoxycarbonyl-4-chlorotrifluoromethanesulfonanilide and 100 parts by weight of camphor are pressed under a pressure of 5 kg/cm$^2$ to give a tablet.

Production Example 3

A mixture of five parts by weight of 2-methoxycarbonyl-4-chlorotrifluoromethanesulfonanilide and 100 parts by weight of naphthalene are pressed under a pressure of 5 kg/cm$^2$ to give a tablet.

Production Example 4

A mixture of five parts by weight of 2-methoxycarbonyl-4-chlorotrifluoromethanesulfonanilide and 100 parts by weight of p-dichlorobenzene are pressed under a pressure of 5 kg/cm$^2$ to give a tablet.

Production Example 5

A mixture of five parts by weight of 2-methoxycarbonyl-4-chlorotrifluoromethanesulfonanilide and 100 parts by weight of crystallized cellulose (avicel; manufactured by Asahi Chemical Industry Co., Ltd.) are pressed under a pressure of 5 kg/cm$^2$ to give a tablet.

Next, the Test example shows the method for controlling acarina of the present invention.

Test Example 1

The tablet (1 g) produced in each of Production examples 1–5 was set on an aluminum plate (diameter; 3.5 cm). The plate was put in a 200 cm$^3$ plastic case. On the other hand, two aluminum plates (diameter; 3.5 cm) were spread on by filter paper, which is surrounded by adhesives for preventing mites from running away, and 20 to 50 house dust mites (*Dermatophagoides farinae*) were released on the plates. Then a cup holding an aqueous solution saturated with ammonium nitrate was positioned on the bottom of the plastic case to maintain humidity, and was then closed. After 4 days, the house dust mites were observed on a microscope, and confirmed that the acaricidal percentage was 100%.

What is claimed is:

1. A method for controlling acarina which comprises setting at least one tablet obtainable by pressing 2-methoxycarbonyl-4-chlorotrifluoromethanesulfonanilide and at least one vehicle selected from the group consisting of dextrin, crystallized cellulose, calcium hydrogenphosphate, calcium carbonate, starch, lactose, camphor, naphthalene, trioxane and p-dichlorobenzene, in a small space.

2. The method according to claim 1, wherein the small space is less than 50 m$^3$.

3. The method according to claim 2, wherein the small space is selected from the group consisting of drawers, a closet, a lumber room, cases, a stuffed doll, bed clothes, and a chest.

4. The method according to claim 1, wherein 0.1 to 200 g of 2-methoxycarbonyl-4-chlorotrifluoromethanesulfonanilide per 1 m$^3$ of the small space is used.

5. The method according to claim 1, wherein the 2-methoxycarbonyl-4-chlorotrifluoromethanesulfonanilide is present at 0.5 to 100 wt % in the tablet.

6. An acaricidal tablet obtainable by pressing a composition containing 2-methoxycarbonyl-4-chlorotrifluoromethanesulfonanilide and at least one vehicle selected from the group consisting of dextrin, crystallized cellulose, calcium hydrogenphosphate, calcium carbonate, starch, lactose, camphor, naphthalene, trioxane and p-dichlorobenzene.

7. The tablet according to claim 6, wherein the 2-methoxycarbonyl-4-chlorotrifluoromethanesulfonanilide is present at 0.5 to 100 wt % in the tablet.

* * * * *